United States Patent [19]

Crossway et al.

[11] Patent Number: 4,996,144

[45] Date of Patent: Feb. 26, 1991

[54] MICROASSAY FOR DETECTION OF DNA AND RNA

[75] Inventors: Anne Crossway, Davis; Catherine M. Houck, Vacaville, both of Calif.

[73] Assignee: Calgene, Inc., Davis, Calif.

[21] Appl. No.: 694,715

[22] Filed: Jan. 25, 1985

[51] Int. Cl.$^5$ .............................................. C12Q 1/68
[52] U.S. Cl. ...................................... 435/6; 436/501; 935/77; 935/78
[58] Field of Search ............. 436/501; 435/6; 935/77, 935/78

[56]  References Cited
U.S. PATENT DOCUMENTS

| | | | |
|---|---|---|---|
| 4,483,920 | 11/1984 | Gillespie et al. | 935/78 X |
| 4,670,399 | 6/1987 | Okubara et al. | 435/172.3 X |
| 4,745,057 | 5/1988 | Beckage et al. | 435/91 X |
| 4,762,780 | 9/1988 | Spector et al. | 436/6 |
| 4,837,148 | 6/1989 | Cregg | 435/172.3 |

OTHER PUBLICATIONS

Gianfranceschi, G., et al., Biol. Abst. 71(1):406, Abstract No. 3908.
Brandsma, J., et al., Proc. Natl. Acad. Sci., 77, No. 11:6851–6855 (1980).
Howell, S. H., et al, Virology 86:468–481 (1978).
Scalenghe, F., et al. Chromosoma (Berl.), 82:205–216 (1981).
Collins, P. L., et al., Journ. Virol., 28, No. 1:324–336, (1978).

*Primary Examiner*—Esther L. Kepplinger
*Assistant Examiner*—Laurie A. Scheiner
*Attorney, Agent, or Firm*—Barbara Rae-Venter; Bertram I. Rowland

[57]  ABSTRACT

A novel hybridization diagnostic technique is involved employing micromanipulation of cells for detection of DNA or RNA in the cells. Cellular suspensions are employed, the DNA or RNA purified by microextraction using liquid media having differential solubilization properties, whereby the nucleic acid is retained in an aqueous microdrop. The nucleic acid in the microdrop may then be assayed with a nucleic acid probe in accordance with conventional ways.

7 Claims, No Drawings

MICROASSAY FOR DETECTION OF DNA AND RNA

BACKGROUND OF THE INVENTION

1. Field of the Invention

There are many situations where one wishes to detect a minor amount of DNA in a small population of cells. This situation is particularly applicable to transformation of cells, where the multiplication of the cells is relatively slow, so that the availability of a sufficient number of cells to provide for a sufficient amount of the nucleic acid to be able to detect in ordinary samples may take days, weeks or months. Illustrative of such situations, where long periods of time may be involved, is the situation with transformation of plant cells where several weeks or months may be involved to obtain a sufficient amount of tissue culture to perform a Southern or Northern hybridization analysis. An additional example would be a case where an assay for transient expression is desired in cells microinjected with DNA or RNA. An immediate assay would allow for monitoring of the fate of injected nucleic acids as well as detection of transcription from injected DNA molecules. Therefore, techniques which allow for hybridizations with a small number of cells can be of great interest and importance in these situations.

2. Description of the Prior Art

Hybridization techniques are described in Thomas, Proc. Natl. Acad. Sci. USA (1980) 77:5201–5205; White and Bancroft, J. Biol. Chem. (1982) 257:8569–8572; and Manzari et al., Proc. Natl. Acad. Sci. USA (1983) 80:11–15. See also Maniatis et al., (1982) Molecular Cloning, A Laboratory Manual, Cold Spring Harbor Laboratory, Cold Spring Harbor, New York, pp. 309ff. Techniques describing hanging drops include Edstrom, (1964) In: Methods in Physiology (D. M. Prescott, ed.) New York, Academic Press, pp. 417–447 and Scalenghe et al., Chromasoma (Berl.) (1981) 82:205–216.

SUMMARY OF THE INVENTION

A small number of cells in a drop of a polyol solution are placed under oil, excess polyol solution mechanically removed, proteins hydrolyzed with a protease solution under denaturing conditions at moderate temperatures, the organic soluble cell debris removed by extraction with organic medium, followed by addition of a mildly polar organic solvent which disperses the solubilizing organic medium into the surrounding oil medium to leave an aqueous drop containing nucleic acids which can be transferred to a filter for hybridization.

DESCRIPTION OF THE SPECIFIC EMBODIMENTS

In accordance with the subject invention, a microhybridization assay technique is provided, where nucleic acid, DNA or RNA, can be assayed with fewer than 500 cells, conveniently with fewer than 200 cells, and generally from 1 to 100 cells, if necessary from about 1 to 50 cells.

The method involves employing cells which are or can be readily dispersed and can be obtained as suspensions of individual cells. Any cell type can find use in the subject method where cells have a cell wall, desirably the cell wall is removed to provide protoplasts or spheroplasts.

When protoplasts are used, the first step involves removing the cellular wall. The method then involves dispersing the cells to be assayed in a polyol solution submerged under a hydrocarbon-like liquid, generally a paraffin oil. Excess polyol solution is removed and proteins solubilized in a denaturing solvent with a protease at mildly elevated temperatures. After the cells have been deproteinized, the debris is solubilized in an organic solvent. This is followed by the addition of a second more polar organic solvent, which results in the dispersion of the first organic solvent into the hydrocarbon-like liquid medium leaving a small clear drop containing nucleic acids, which may be micromanipulated and transferred to a substrate, e.g. a support for hybridization.

Each of the steps will now be considered in detail. It should be understood that in most cases, alternative media may be employed without significant change in the efficiency of the method. However, the materials employed have been found to be successful and are those which are generally used in the preparation of nucleic acid samples for hybridization.

For protoplast formation, the cells to be analyzed are combined with polysaccharidases to remove the cell wall to produce protoplasts or spheroplasts. The enzyme reagent employed is either a single or mixture of saccharidases, such as cellulase, pectolyase, zymolyase, glucanase, and the like. Depending upon the particular enzyme, the concentration of the enzyme will generally vary, being in the range of about 0.001 to 1 weight percent. Desirably, included in the aqueous medium is a polyol of from about 4 to 7, more usually from about 5 to 6 carbon atoms, having from 4 to 7 hydroxyl groups, preferably a ratio of 1 hydroxyl to 1 carbon atom. Of particular interest is sorbitol. The polyol may be present in from about 5 to 20 weight percent, preferably from about 10 to 15 weight percent, more preferably about 10 weight percent. Depending upon the particular cell, either spheroplasts or protoplasts are obtained.

The cells which are employed may be prokaryotes or eukaryotes and may be obtained from a wide variety of sources. Of particular interest will be eukaryotes, generally eukaryotes other than unicellular microorganisms, such as yeast. Among the eukaryotic cells of interest are those from plants, mammals, insects, birds, etc.

A microdroplet is obtained from the medium containing the cells to be assayed. The microdroplet is transferred to a depression containing a hydrocarbonlike oil. The transfer can be achieved with a transfer pipette connected by appropriate tubing to a micrometer syringe. The subsequent manipulations are carried out in a depression slide in which is present a hydrocarbonlike liquid, particularly a paraffin oil. The depression is substantially filled with the hydrocarbon-like liquid and from about 1 to 10, usually 2 to 5 microdrops of 1-20 nanoliter volumes containing the cells and some medium are transferred to the depression. The amount of the hydrocarbon-like liquid will be one of convenience, generally less than about 2 ml, usually about 1 ml or less. The polyol suspension will usually be less than about 0.1 $\mu$l, more usually less than about 0.01 $\mu$l.

Micropipettes are employed for subsequent manipulations, where the tip diameter is from about 5 to 10 $\mu$. The micropipettes are back-filled with the appropriate reagents prior to insertion in the micromanipulators for manipulation.

The subject cells may be filtered, depending upon their source to ensure the absence of clumping. After filtration, in order to concentrate the cells, the cells may be centrifuged in an aqueous polyol solution, comparable to the medium employed for the cell wall removal, followed by suspension at a relatively high density $10^4$ to $10^6$ cells/ml, in a comparable medium.

Drops having the desired number of cells are transferred to the depression containing the hydrocarbonlike oil and any excess of the medium removed employing a micropipette. The drop is then refilled with a medium containing a protease and denaturant, e.g., sodium dodecylsulfate, under conditions where there is cell breakdown and solubilization. Temperatures for the enzymatic degradation will generally range from about room temperature to 40° C., preferably from about 35° to 40° C., and the concentration of protease may be varied widely, depending upon the nature of the particular protease, the temperature employed, the time involved, and the like.

Generally, from about 100 to 500 μg/ml of the protease will be satisfactory. Of particular interest are endoproteases, such as proteinase K. The medium will be selected to optimize the activity of the protease, generally having a pH of from about 7 to 8 and having varying other materials, such as buffer, chelators, salt, and the like, where each of the additives will be present in from about 10 to 200 mM and the denaturant will generally be present in from about 0.05-0.2%. Usually, 1 to 24 hours will suffice for solubilization.

A solvent may then be employed which is substantially insoluble in the hydrocarbon-like phase and sparingly soluble in the aqueous phases, so as to form a separate phase distinct from the aqueous phase and from the hydrocarbon-like liquid into which the cell debris will be transferred. Preferably, a phenolic compound is employed, particularly of from 6 to 9 carbon atoms, more particularly phenol. These solvents are characterized by being insoluble in a paraffin oil, but soluble in the subsequently employed solvent usually a halohydrocarbon. Excess phenol is employed and shrinking and darkening is observed as the cell debris and other organic soluble components are extracted into the phenolic layer. The amount of phenol necessary to cover the drop will usually be in the range of 0.5-3, more usually about 1-3× the volume of the polyol suspension.

When bubbles are observed, the excess phenol is removed and to the phenolic layer is added a mixed halohydrocarbon-alkanolic solvent, where the alkanol is of from 4 to 6, preferably 5, carbon atoms, and is present in about 1 to 6, preferably about 2 to 5 volume percent. Upon addition of the mixed solvent, the phenolic compound and the mixed solvent become miscible with the hydrocarbon-like liquid. Clearing and expansion of the aqueous drop occurs. The mixed solvent is used as a wash, and about 1-10× the volume of phenol is employed.

After clearing of the aqueous drop containing the nucleic acid, the drop may be subjected to further treatment or may be directly transferred to a substrate for assay. Further treatment may include enzyme digestion of one or the other of RNA or DNA, depending upon the nucleic acid to be analyzed. Enzymes such as DNase or RNase may be employed in accordance with conventional techniques to degrade the undesired nucleic acid. To aid in the disruption of nucleic acid secondary structures, formamide may be added so as to provide up to about a 50% formamide solution followed by heating. Other treatments may include treatment with nickase to disrupt circular structures, mixing with nucleic acid to enhance transfer efficiency, treating with formaldehyde or urea to disrupt secondary structures.

Various supports may be employed for binding the DNA for hybridization. Supports include nitrocellulose, Gene Screen (NEN), Gene Screen Plus (NEN), Nytran (S+S), nylon 66, etc.

Standard hybridization conditions may be employed, initially employing prehybridization with 0-80% formamide, 5 to 10× SSC, 533 Denhardt's medium, and such other additives as SDS, EDTA, buffer, e.g., phosphate buffer, at a pH of about 6 to 7, and denatured DNA. The support containing the microdot(s) may be incubated for from about 1 to 6 hours at elevated temperatures, generally from about 30° to 80° C. in vacuo to fix the nucleic acid to the support.

Various probes may be used, which may be labeled or unlabeled, depending upon the method of detection. For example, antibodies can be prepared which are specific for double-stranded as compared to singlestranded nucleic acid. These antibodies may then be used to detect duplex formation. Usually however, a labeled probe will be employed, where any convenient label may be employed, such as a radionuclide, ligand, enzyme, fluorescer, or the like. Conveniently, a ligand may be employed such as biotin, which is covalently bonded to the probe. After duplex formation, avidin may be added which has a label providing a detectable signal, such as a radionuclide, enzyme, or fluorescer, which will only bind to the biotin bound to the support through the duplex. In this manner, duplex formation may be detected. Probes may be denatured by boiling for 5 min. and then added to the hybridization solution, which differs from the prehybridization solution by containing dextran sulfate, or other volume excluding agent. After hybridizing at preselected conditions, generally from about 1 to 24 hours at temperatures from about 25° to 60° C., the filters may be washed in solutions providing for the same or more stringent conditions than the hybridization. In this manner, non-specifically bound nucleic acids may be removed. Label remaining bound to the support may then be detected as indicative of the presence of a particular sequence.

The following examples are offered by way of illustration and not by way of limitation.

EXPERIMENTAL

Plant Material

Plants of *Brassica campestris* ssp. *rapa* var. Just Right were grown from seed in a greenhouse. When plants reached the four leaf stage, they were inoculated with CaMV strain CM4-184, derived from pCaMV20 DNA inoculation (Howarth et al., *Virology* (1981) 112:678–685). The surface of one leaf on each plant was dusted with carborundum, then abraded by rubbing the surface with a leaf taken from a previously infected plant. Some of the plants were maintained without inoculation for use as uninfected controls.

Protoplasts were prepared from both uninfected and CaMV infected leaves when symptoms were clearly visible (about 3 weeks from date of inoculation). Leaf pieces were incubated for 4hr at 3° C. in darkness in an enzyme mixture containing 0.4% cellulase RS, 0.025% pectolyase Y23 and 10% sorbitol, pH 5.8. Leaves were not peeled, but were infiltrated for several minutes at 200 mTorr. Protoplasts were separated from undigested material by filtration through a 300 μ filter. Following two centrifugations at 37×g in 10% sorbitol, the protoplasts were suspended in 10% sorbitol and individual cells were selected.

Transfer

One to 50 protoplasts were selected from the protoplast suspensions using a Nikon stereozoom microscope. Selection and transfer of protoplasts in paraffin oil-filled depression slides was performed with a transfer pipette connected by plastic tubing to a micrometer syringe. Depression slides were made by gluing a siliconized cover slip over a square hole cut into a plexiglass slide. Transfer pipettes were hand-pulled over a Bunsen burner from a 1.2 mm O.D. glass tubing. Four microdrops of nanoliter volumes containing the selected protoplasts plus some sorbitol were formed in each depression.

The microextraction procedure was performed in the depression slide after mounting on a Leitz Diavert microscope. Leitz micromanipulators were used to position the micropipettes during the extraction. Micropipettes were pulled on a pipette puller (Ultrafine, Frederick Haer and Co.) from Leitz 520-119 glass capillary tubing which had been previously siliconized. Pressure within the micropipettes was controlled through oil-filled plastic tubing connected to Hamilton syringes. The tips of the micropipettes were broken off to a diameter of approximately 5–10 $\mu$ prior to use by touching against a pair of tweezers. Micropipettes were back-filled with chemicals prior to insertion in the micromanipulators.

Microextraction Protocol

Excess sorbitol was removed from each microdrop with a micropipette (B). The drop was then refilled with a protease K/SDS solution (100 mM Tris, pH 7.5; 12 mM EDTA; 50 mM NaCl; 0.1% SDS; 200 $\mu$g/ml Proteinase K). Immediate breakdown of the protoplasts was evident at the point of entry. After overnight incubation of the whole slide at 37° C., all the protoplasts were observed to have been solubilized. Excess phenol was then layered onto the drop, forming a separate phase between the aqueous drop and the liquid paraffin. During the extraction, shrinkage and darkening of the drop occurred with movement of cell debris into the phenol layer. When bubbles were observed in the phenol layer most of the phenol was removed with a micropipette, and the drop was then washed extensively with chloroform/isoamyl alcohol (24:1). Turbidity was seen at the point of contact of the chloroform solution with the phenol layer. During the chloroform wash, the phenolic layer was gradually dispersed into the surrounding oil resulting in clearing and expansion of the aqueous drop. When the phenol layer was completely dispersed, the drop containing nucleic acids was either transferred directly to a Gene Screen (New England Nuclear) filter or was further treated as outlined below. Microdrops treated as above are hereafter referred to as having had the standard treatment.

Additional digestion to allow differential detection of DNA or RNA can be done. For the detection of RNA only, the drop was treated with DNase by adding an equal volume of DNase solution (50 mM Tris, pH 7.5; 50 mM NaCl; 50 mM MgCl$_2$; 1 mM dithiothreitol; 2 Units/ml RNasin, Promega Biotec; 60 $\mu$g/ml Deoxyribonuclease I, Worthington DPFF) followed by incubation at 37° C. for 1 hour. For the detection of DNA only, the drop was treated with RNase by adding an equal volume of RNase solution (10 mM Tris, pH 7.5; 15 mM NaCl; 200 $\mu$g/ml Ribonuclease A, Sigma Type XIIA) followed by incubation at 37° C. for 1 hour. To aid in the disruption of nucleic acid secondary structures, some drops were further treated with formamide. Formamide was added to increase the size of the drop approximately two-fold, resulting in a final concentration of at least 50% formamide. The slide was then incubated at 42° C. for 30 min. The microdrops containing nucleic acids were then picked up with a micropipette and placed on a dry Gene Screen filter. The filters were baked for 2 hours at 80° C. in a vacuum oven.

Hybridization

Standard hybridization conditions were essentially as outlined in Maniatis et al., (1982) *Molecular Cloning, A Laboratory Manual*, Cold Spring Harbor Laboratory, Cold Spring Harbor, N.Y. Prehybridization of the filters was done in 5 X SSC (1 X SSC is 0.15 M NaCl, 0.015 M sodium citrate); 0.1% SDS; 5 mM EDTA; 5 X Denhardt's solution; 25 mM sodium phosphate buffer, pH 6.5; 50% formamide; and 200 $\mu$g/ml denatured salmon sperm DNA for approximately 4 hours at 42° C. The plasmid pCaMV10 which contains a full-length copy of the CaMV strain CM1841 cloned at the SalI site of pBR322, Gardner et al., *Nucleic Acids Res.* (1981) 9:2871–2887, was used as a probe. Probes were labelled by nick translation using reagents from BRL and $^{32}$P dCTP 2000 Ci/mmole (New England Nuclear) followed by Sephadex G-75 chromatography to remove unreacted nucleoside triphosphates. The resulting DNA generally had a specific activity of approximately $10^8$ cpm/$\mu$g. The probe was denatured by boiling for 5 min. and added to the hybridization solution (prehybridization solution containing 10% dextran sulfate). Filters were hybridized at 42° C. for at least 12 hours. The filters were washed at 60° C. in 1 X SSC and 0.1% SDS for 30 min. followed by three 30 min. washes at 60° C. in 0.1×SSC and 0.1% SDS. Autoradiography was performed using Kodak XAR film and a Dupont Cronex intensifying screen for approximately 3 days.

Hybridization Standards

Each hybridization was accompanied by a filter containing standards made from known quantities of pCaMV10 DNA. These filters were made by dotting 1 $\mu$l samples of serial dilutions of purified pCaMV10 DNA onto dry Gene Screen filters which were then baked for 2 hours in an 80° C. vacuum oven. Dilutions were routinely made into 0.5M NaOH although no difference was observed when dilutions were made into 50% formamide. In addition, standard dilutions of plasmid DNA were used to compare the sensitivity of the hybridization using nitrocellulose filters (Schleicher and Schuell BA85) and Gene Screen Plus (New England Nuclear) filters. The hybridization signal using nitrocellulose filters was not as strong as the Gene Screen signal. The Gene Screen Plus hybridization using a slightly different hybridization protocol recommended by the vendor had greatly increased background which did not allow the relatively long (3 day) exposures necessary for the detection of signals from small numbers of cells. In addition, drops deposited on dry Gene Screen Plus tended to distort due to nonuniformity of the paper surface. Drops containing 10 protoplasts each were subjected to various treatments as previously described. The following indicates the various treatments.

A. A standard dilution series of alkaline denatured (0.5 M NaOH) pCaMV DNA. One µl of each dilution was dotted onto Gene Screen.

| Dot 1. | 3000 | pg |
| --- | --- | --- |
| Dot 2. | 300 | pg |
| Dot 3. | 30 | pg |
| Dot 4. | 3.0 | pg |
| Dot 5. | 0.30 | pg |
| Dot 6. | 0.15 | pg |

B. and C. A series of four dots, each made from ten protoplasts from uninfected and CaMV-infected B. campestris ssp. rapa leaves, respectively.

| Dot 1. | Standard treatment |
| --- | --- |
| Dot 2. | Standard treatment plus RNase |
| Dot 3. | Standard treatment plus formamide |
| Dot 4. | Standard treatment plus DNase and formamide. |

D. and E. Replica of Filter B and C, respectively.

F. and G. Replica of Filter B and C, respectively.

Several replica filters were made on different days using protoplasts from infected and uninfected leaves. Filters B, D, and F were made using uninfected cells and none of the dots show detectable hybridization to the pCaMV10 probe. Filters C, E, and G were made using infected cells and show hybridization to the CaMV probe. The quantity of nucleic acid extracted from each drop was estimated by comparison of the hybridization intensity with standard dilutions of denatured pCaMV10 DNA (Filter A).

Dot 1 on each filter received the standard treatment with no nuclease or formamide steps. Hybridization of these dots is expected to result from RNA that lacks significant secondary structure or DNA that has been partially denatured during the extraction of baking procedure. The intensity of the signal of dot 1 from filters C, E, and G is approximately the same as the signal from 1.5 pg of purified plasmid DNA. If the hybridization were all due to CaMV DNA (MW=$5.3 \times 10^6$ daltons), this would correspond to 170,000 molecules or 17,000 molecules per cell. If the hybridization were all due to CaMV RNA (average MW=$1.6 \times 10^6$ daltons), this would correspond to 560,000 molecules or 56,000 molecules per cell.

The second dot on each filter received the standard treatment plus RNase. Hybridization here is expected to result only from DNA which is partially denatured either in the cell or as a result of the treatment. The intensity (Filters C, E, and G, dot 2) corresponds to approximately 0.3 pg or 3,400 molecules per cell. This should be compared with the estimated 1,000,000 CaMV viral particles (10 pg) found in an infected cell. It may be that this small amount of hybridization results from partially single stranded DNA molecules that are present in infected cells.

The third dot of each set received the standard treatment plus formamide under conditions (42° C., 50% formamide) that might be expected to disrupt short stretches of secondary structure in the single stranded RNA molecules and where partial denaturation of the DNA might also occur upon baking. The intensity of hybridization in this case (Filters C, E, and G, dot 3) corresponds to approximately 3 pg which would be the equivalent of 34,000 molecules per cell of DNA or 110,000 molecules per cell of RNA. Comparing this result to dot 1 shows that the hybridization signal has increased approximately ten fold due to this denaturation step. However, the levels are still approximately 30-fold lower than would be expected from the known quantities of viral DNA in the infected cells. This could either be because the DNA is not completely denatured or because DNA in viral inclusion bodies is not extracted well by this method. It is unlikely that denaturation is the problem because similar hybridization intensities were obtained when standard treatment was followed by denaturation in 0.5 M NaOH for one hour at room temperature. It has been reported that DNA from viral inclusion bodies is difficult to extract in a total cellular DNA preparation (Hull and Covey, *Nucleic Acids Res.* (1983) 11:1881-1895) and it is possible that the DNA from viral inclusion bodies is not all available for hybridization using our technique.

The fourth dot of each set received the standard treatment plus DNase, and was then denatured with formamide. This treatment is expected to remove any DNA and to denature short stretches of secondary structure in the remaining RNA. The hybridization intensity corresponds to approximately 0.1 pg which is equivalent to 3,700 molecules of RNA per cell. This value is very close to the estimated number of CaMV RNA molecules (2,000) expected in an infected cell (calculated assuming 2% of the polyA mRNA in an infected cell is from CaMV).

The hybridization intensities vary somewhat between the replicate filters. The reason for this is not known, but there are a number of possible explanations. Volumes were estimated by observation of drop expansion, so that volumes may vary resulting in varying extractions and treatment efficiencies. The very small sample size (1-50 cells) means that variations in the size of the individual protoplasts or in the metabolic activity of the individual cells used for different protoplast preparations could result in differences in the quantity or in the conformation of the viral nucleic acids in different drops. The amount of denaturation of the nucleic acids under the subject conditions could be variable. The non-specific nuclease activity in the RNase and DNase preparations may be sufficient to partially degrade the small quantities of RNA or DNA present. This last possibility was tested by RNase or DNase treatment of standard dilution series of CaMV DNA and RNA which showed a reduction in the hybridization signal after nuclease treatment. Increasing the number of cells per microdrop overcomes this problem (up to 50 cells per drop have been used successfully).

It is evident from the above results that extremely small numbers of cells can be employed for detection of nucleic acids. The subject method allows the detection of a few thousand copies of a DNA sequence which may be present in only a few cells, as few as 50 cells or fewer. Thus, where only a few cells are available, rather than requiring extended periods of time which may be necessary to expand the cell population, one can screen the cells and obtain a result in a substantially shorter period.

Although the foregoing invention has been described in some detail by way of illustration and example for purposes of clarity of understanding, it will be obvious that certain changes and modifications may be practiced within the scope of the appended claims.

What is claimed is:

1. A method for detecting a nucleic acid sequence present in a cell population of fewer than 500 cells, said method comprising:
    transferring an aqueous polyol suspension of cells to a paraffin oil and removing any excess of said aqueous polyol;
    solubilizing said cells with a proteinase;
    adding a phenolic extractant to extract cell debris away from the nucleic acid containing aqueous layer and into the phenolic layer;
    adding an alkanolic chloroform solution, whereby the phenolic layer becomes dispersed into the paraffin oil;
    transferring the remaining aqueous drop containing the nucleic acid to a substrate; and
    detecting any of said aqueous bound to said substrate.

2. A method according to claim 1, including the additional step of prior to transferring, enzymatically degrading RNA.

3. A method according to claim 1, wherein said cells have cell-walls and said cell-walls are removed prior to said transferring to said paraffin oil layer.

4. A method according to claim 3, wherein said cells are plant cells.

5. A method for detecting a nucleic acid sequence present in a cell population of from about 1 to 100 cells, said method comprising:
    transferring a cell suspension concentrate of from about 1 to 100 cells in an aqueous sorbitol medium, said sorbitol being present in from about 5 to 20 weight percent to a depression containing a substantially larger volume of a paraffin oil and removing any excess of the aqueous medium to form a droplet;
    solubilizing said cells in said droplet with a proteinase;
    adding sufficient amount of phenol to substantially cover said droplet;
    washing said droplet with an isoamyl alcohol containing chloroform solution whereby said phenol is dispersed in said paraffin oil;
    transferring the remaining aqueous droplet to a substrate: and
    detecting any of said aqueous bound to said substrate.

6. A method according to claim 5, wherein said cells are plant cell protoplasts.

7. A method according to claim 5, wherein said substrate is a support for hybridization.

* * * * *